United States Patent [19]

Mansfield

[11] 4,066,528
[45] Jan. 3, 1978

[54] ANALYTICAL APPARATUS

[75] Inventor: John Rickard Mansfield, Middlesbrough, England

[73] Assignee: Imperial Chemical Industries Limited, London, England

[21] Appl. No.: 706,555

[22] Filed: July 19, 1976

[30] Foreign Application Priority Data

July 30, 1975 United Kingdom ............... 31927/75

[51] Int. Cl.² ............................................. G01N 27/44
[52] U.S. Cl. ............................. 204/195 T; 204/195 S; 204/1 T
[58] Field of Search ............................ 204/1 M, 195 T

[56] References Cited

U.S. PATENT DOCUMENTS

| 2,886,496 | 5/1959 | Eckfeldt | 204/195 T |
| 3,341,430 | 9/1967 | Wickerham et al. | 204/195 T |
| 3,441,490 | 4/1969 | Johansson | 204/195 T |
| 3,563,875 | 2/1971 | Coulson | 204/195 T |
| 3,647,668 | 3/1972 | Lindblad et al. | 204/195 T |

Primary Examiner—T. Tung
Attorney, Agent, or Firm—Cushman, Darby & Cushman

[57] ABSTRACT

Apparatus for coulometry comprises (a) an instrumentation amplifier acting as a differential to single-ended potential convertor having high input impedence, (b) means for feeding (a) with the potential between the sensor and reference electrodes of a coulometric cell and (c) and differential potential input amplifier fed by (a) and by means for setting the output of (c) to zero, the phase shift of the apparatus being less than 90°.

6 Claims, 1 Drawing Figure

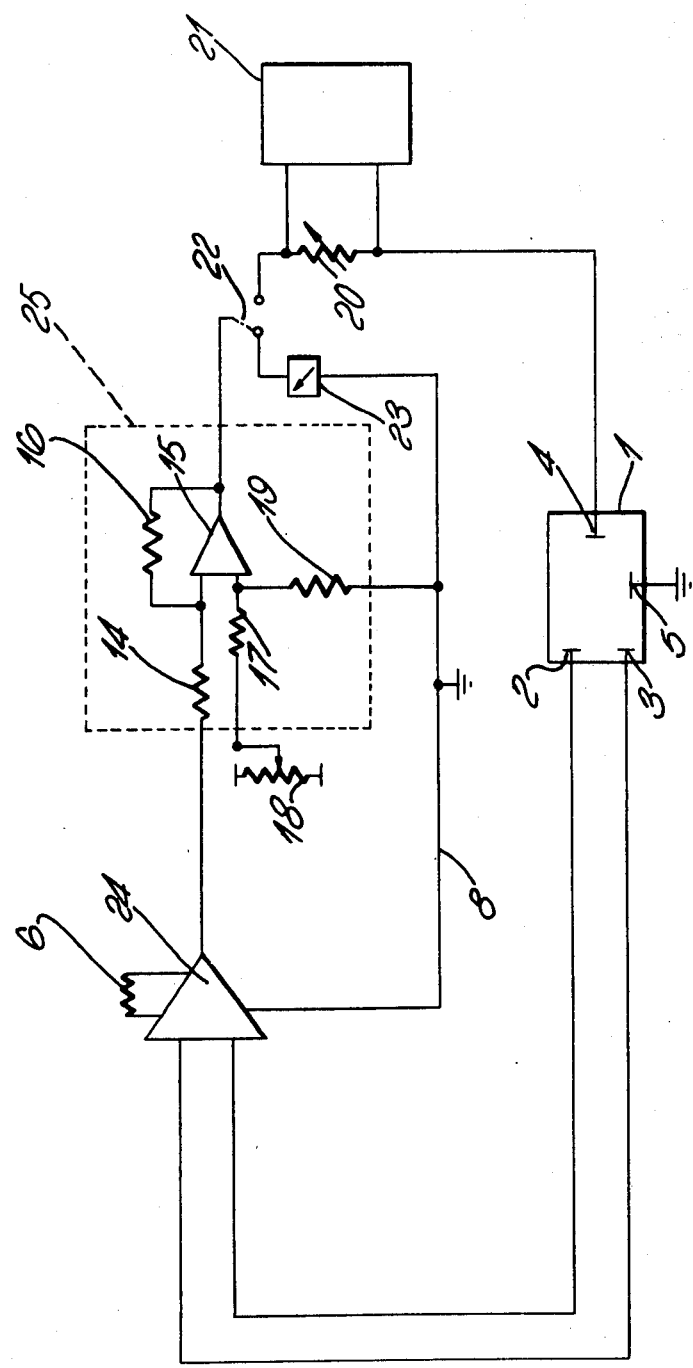

ANALYTICAL APPARATUS

This invention relates to analytical processes and apparatus for performing them, especially to analytical processes carried out by coulometry.

In the analysis of materials by coulometry a sample may be introduced into an electrolyte and a quantity of a material to be determined which is present in the sample may be found by carrying out in the electrolyte an electrolytic process which consumes the material directly or indirectly. The quantity of electricity passed is a measure of the quantity of the material present.

The electrolyte may be a solid or liquid electrolyte. The presence and consumption of such materials may conveniently be sensed in many cases as a variation in the potential difference between a sensor electrode present in the electrolyte and a reference electrode which is in electrolytic communication with the electrolyte. When this potential difference departs from a desired value a current is passed between a generator electrode, which is in the electrolyte and generates a species which consumes the material to be determined, and either the reference electrode or an auxiliary electrode which is in electrolytic communication with the electrolyte but prevents species generated at it from reaching the generator electrode. It may be isolated from the generator electrode geometrically, for example, using a porous barrier or membrane. If the current is passed between the generator and the reference electrodes and the species generated at the reference electrode is hydrogen, the reference electrode may suitably be a palladium electrode as this absorbs hydrogen.

In a process of coulometric determination of a material introduced into an electrolyte the presence of the material may, if desired, be sensed continuously during addition of the material as a variation in the potential difference (the detection potential) between a sensor electrode present in the electrolyte and a reference electrode which is in electrolytic communication with the electrolyte and a sufficient current may be passed between a generator electrode which generates a species which consumes the material and is located in the electrolyte and an electrode which is adapted to prevent species generated at it from reaching the generator electrode, and is the reference electrode or an auxiliary electrode which is in electrolytic communication with the electrolyte, to maintain the detection potential at substantially its initial value.

It is found that by continuously consuming the material as it is added side effects which may arise from the presence of free material in the electrolyte may be avoided and accuracy of the analysis thereby improved and a particularly rapid performance of the analysis is also secured.

The current passing through the generator electrode may suitably be displayed graphically or recorded electronically, for example as an integrated signal displayed in analogue or digital form.

The invention comprises apparatus for carrying out coulometric analysis which comprises:
a. an instrumentation amplifier which acts as a differential to single ended potential convertor having a high input impedance.
b. means for feeding (a) with the potential between the sensor and reference electrodes of a coulometric cell,
c. a differential potential input amplifier fed by (a) and by means (for example, a potentiometer) for setting the output current of (c) to zero at a desired potential difference between the sensor and reference electrodes by feeding a suitable offset potential to (c), the whole apparatus (excluding any coulometric cell) having a phase shift of less than 90° and responding to direct or low frequency electromotive force input signals.

The invention also provides apparatus as aforesaid which comprises an electrolytic cell for holding an electrolyte, means to introduce sample to the electrolyte, a sensor electrode, a reference electrode and a generator electrode, and optionally an auxiliary electrode which is in electrolytic communication with the electrolyte and is adapted to prevent species generated at it from reaching the generator electrode and apparatus as aforesaid to pass current continuously through the generating electrode at all times when the potential difference between the sensor electrode and the reference electrode differs from a preset value and thereby to maintain the said potential substantially constant.

In use, the output of the differential potential input amplifier is fed to the generating electrode of a coulometric cell, of which the auxiliary or reference electrode is earthed. The current passing may suitably be recorded by a high input impedence potentiometric recorder which may suitably be provided in parallel with a variable resistance through which the current to the generator electrode is fed. Conveniently, a switch may be provided to connect the output of the differential potential input amplifier (c) so that it may be switched through a meter to earth to enable the system to be nulled for a given electrode potential in order to avoid generation of a species capable of consuming the material to be determined during a nulling operation prior to the analysis. Alternatively an auto zero facility may be applied to the differential amplifier (c).

One form of the invention will now be described with reference to the FIGURE which shows a circuit diagram of apparatus according to the invention.

A coulometric cell 1 contains a liquid electrolyte, a sensor electrode 2 in the liquid and a reference electrode 3 in communication with the liquid, a generator electrode 4 in the liquid and an auxiliary electrode 5 in electrolytic communication with the liquid, but geometrically isolated from the liquid by a porous barrier (not shown). The sensor electrode is connected to the non-inverting input of an instrumentation amplifier with a field-effect transistor input 24 and the reference electrode is connected to the non-inverting input of the instrumentation amplifier with a field-effect transistor input 24, the effect of which is to provide a low impedence output from a high impedence input. Any change in potential which is desired may be secured by selecting an appropriate gain resistor 6.

The output of amplifier 24 which is of single-ended potential is fed through resistor 14 to the inverting input of a D.C. amplifier of high temperature stability which is provided with a feed-back through resistor 16. The non-inverting input of differential operational amplifier 15 is fed through resistor 17 with a D.C. potential derived from potentiometer 18 or other D.C. potential reference source and the non-inverting input is also earthed through resistor 19, resistors 17 and 19 together acting as potential dividers. Resistors 14, 17, 19 and 16 cause amplifier 15 to operate in a differential mode.

The output of amplifier 15 is fed through a variable resistor 20 in parallel with a high input impedence potentiometric recorder 21 by means of a switch 22 to generator electrode 4, switch 22 alternatively connecting the output of amplifier 15 through null meter 23 to earth. Auxiliary electrode 5 is earthed.

In use switch 22 is adjusted to connect the output of amplifier 15 through null meter 23 to earth and a sufficient potential applied by potentiometer 18 to produce no current. The output of amplifier 15 is then connected to generator electrode 4 and an analysis is commenced. When a sample enters a liquid electrolyte in the coulometric cell the potential difference between the sensor electrode 2 and the reference electrode 3 is altered and this is converted to a single-ended potential at lower impedance in the instrumentation amplifier 24 which acts as a differential to single-ended potential convertor which causes the differential amplifier 25 to pass current through the generator electrodes until the sensor electrodes return to their initial value.

Using the electronic circuit described with reference to the drawing, together with a standard microcoulometric titration cell for sulphur, containing an aqueous electrolyte of 0.5% potassium iodide and 0.4% acetic acid it was possible to determine less than 10 ng of sulphur as sulphur dioxide in a gas stream.

A sulphur analysis was carried out on a microliter sample of a sulphur containing liquid hydrocarbon, which was pyrolysed in an oxidation pyrolysis furnace using a carrier gas of oxygen and nitrogen to give sulphur dioxide.

The sulphur dioxide containing gas stream was passed into the coulometric titration cell where it reacted with iodine. The current required to regenerate the iodine was directly proportional to the sulphur in the hydrocarbon sample.

We have found that the apparatus can be made to resolve variation in cell potential differences of 1 millivolt or less and to resolve currents of less than 1 microamp.

I claim:

1. Apparatus for carrying out coulometric analysis which comprises:
   a. an instrumentation amplifier which acts as a differential to single ended potential convertor having a high input impedance,
   b. a coulometric cell having a sensor electrode, a reference electrode, and a generator electrode and means for feeding (a) with the potential between the sensor and reference electrodes of said coulometric cell,
   c. a differential potential input amplifier fed by (a) and by means for setting the output current of (c) to zero at a desired potential difference between the sensor and reference electrodes by feeding a suitable offset potential to (c), the whole apparatus excluding the coulometric cell having a phase shift of less than 90° and responding to direct or low frequency electromotive force input signals.

2. Apparatus as claimed in claim 1 in which the means for setting the output of (c) to zero at a desired potential difference between the sensor and reference electrodes by feeding a suitable offset potential to (c) comprises a potentiometer.

3. Apparatus as claimed in claim 1 which further comprises means for holding an electrolyte and means to introduce sample to the electrolyte.

4. Apparatus as claimed in claim 3 in which the coulometric cell further comprises an auxiliary electrode in electrolytic communication with the electrolyte and adapted to prevent species generated at it from reaching the generator electrode.

5. Apparatus as claimed in claim 1 in which the current passing to the generator electrode is recorded by a high input impedance potentiometric recorder which is in parallel with a variable resistance through which current to the generator electrode is fed.

6. Apparatus as claimed in claim 1 in which a switch is provided to connect the output of the differential potential input amplifier (c) to earth through a meter to enable the system to be nulled for a given electrode potential in order to avoid generation of a species capable of consuming the material to be determined during a nulling operation prior to the analysis.

* * * * *